United States Patent [19]

Ichinomiya et al.

[11] Patent Number: 4,721,438

[45] Date of Patent: Jan. 26, 1988

[54] MOTOR-DRIVEN FLUID PUMP

[75] Inventors: Tsutomu Ichinomiya; Koichi Ishino, both of Hikone, Japan

[73] Assignee: Matsushita Electric Works, Ltd., Osaka, Japan

[21] Appl. No.: 38,165

[22] Filed: Apr. 14, 1987

[30] Foreign Application Priority Data

Apr. 24, 1986 [JP] Japan .................................. 61-095164

[51] Int. Cl.⁴ .......................... F04B 39/08; A61B 5/02
[52] U.S. Cl. ...................................... 417/316; 128/685
[58] Field of Search ............... 417/315, 316, 317, 236, 417/238, 510; 604/75; 128/677, 679, 680, 681, 682, 683, 685, 686, 694, 327, 900

[56] References Cited

FOREIGN PATENT DOCUMENTS 40293 9/1985 Japan .................................. 417/316

Primary Examiner—Leonard E. Smith
Attorney, Agent, or Firm—Armstrong, Nikaido, Marmelstein & Kubovcik

[57] ABSTRACT

A fluid pump has a pumping member which defines the boundary of a pump chamber and is driven to reciprocate between the positions of expanding and contracting the pump chamber for drawing in the pump chamber a fluid and feeding it into a vessel to be pressurized thereby. The pumping member is connected to the output shaft of a reversible motor through a driving linkage capable of translating the rotary motion of the output shaft into the reciprocating motion of the pumping member. A release valve is provided in a fluid path between the pump chamber and the vessel for rapidly releasing the pressurized fluid out of the vessel. The release valve is operatively connected to the motor output shaft through a release valve actuator which responds to the reversal of the motor for opening the release valve and has a delay mechanism providing a delayed response action in opening the release valve so that the initiation of opening the release valve is inhibited until the output shaft rotates in the reverse direction through an angle of more than 180 degrees from the reversing point, thereby inhibiting an unintended opening of the release valve due to the reverse translation of the reciprocating motion of the pumping member because of kickback by pressurized fluid in the pump chamber when the motor is stopped.

18 Claims, 31 Drawing Figures

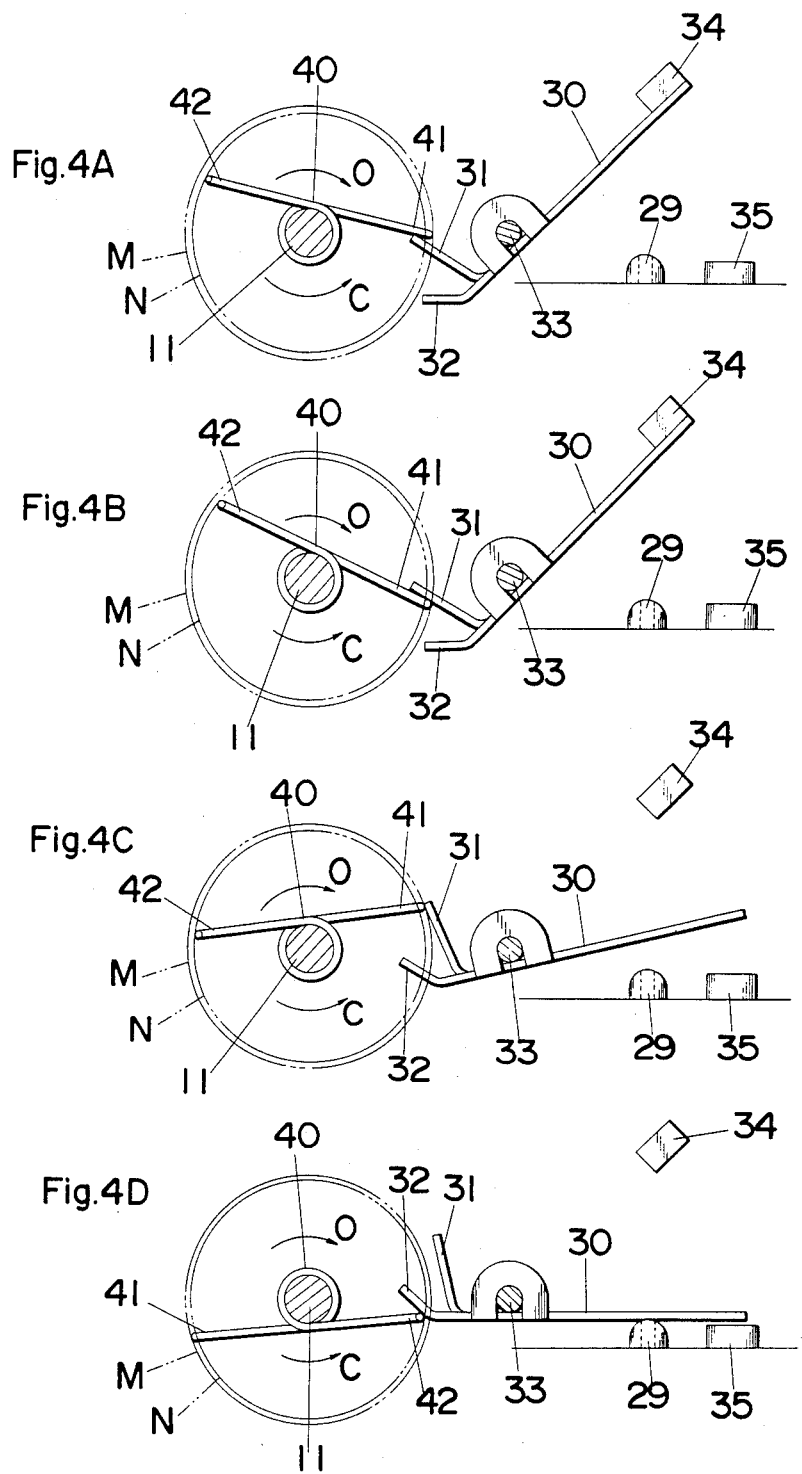

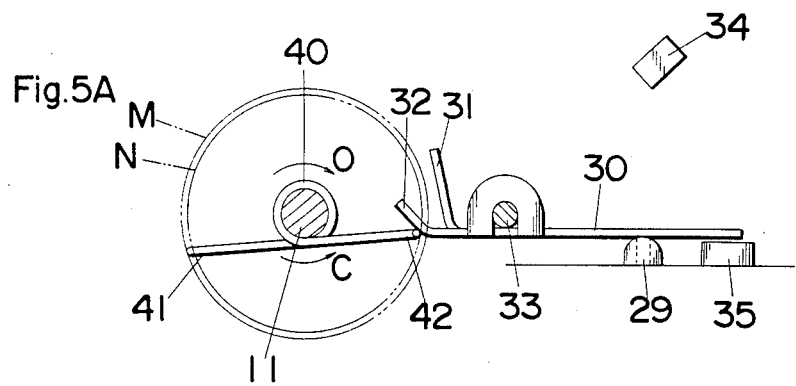
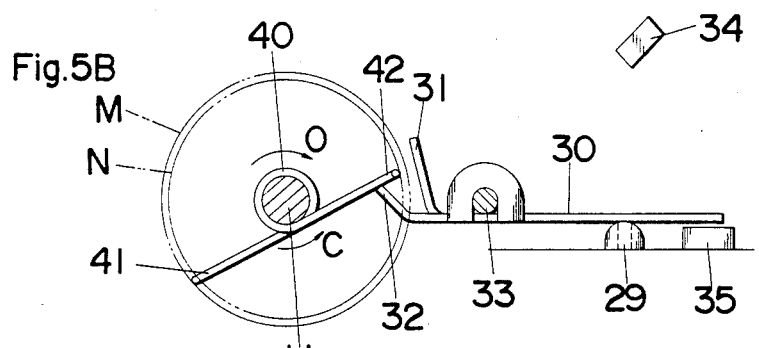
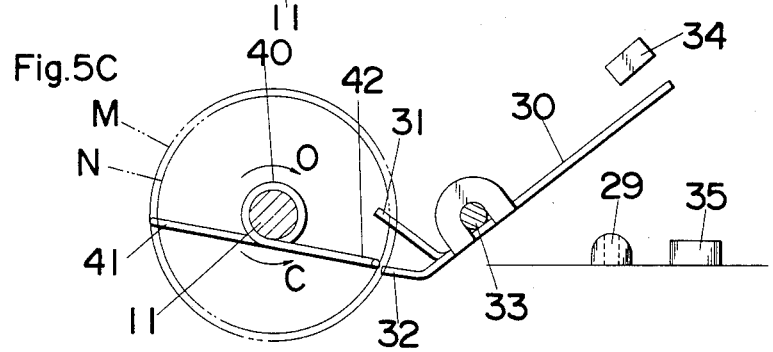
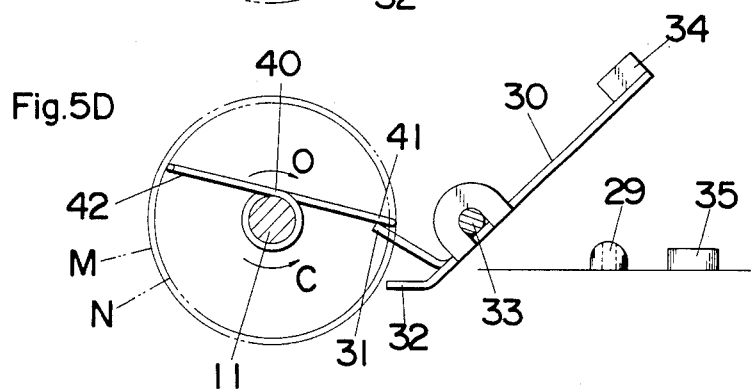

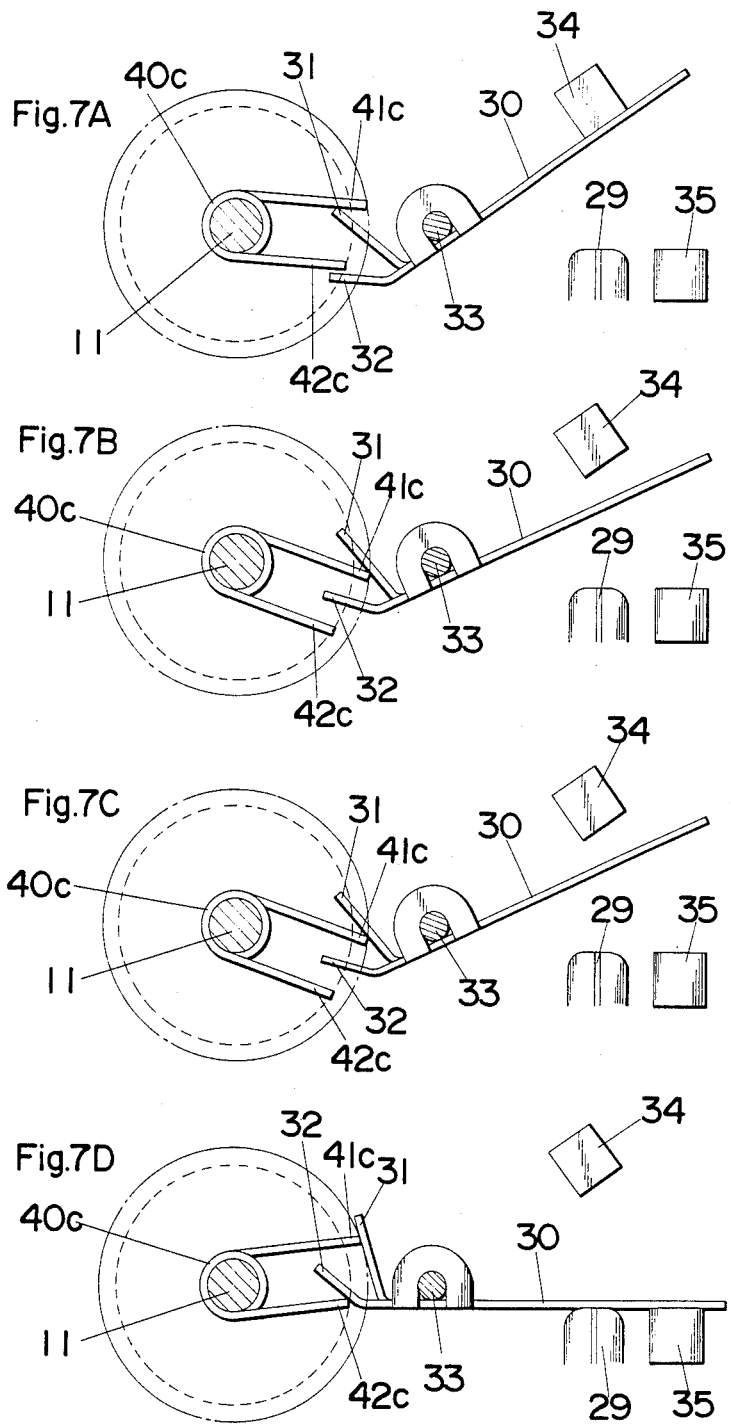

MOTOR-DRIVEN FLUID PUMP

BACKGROUND OF THE INVENTION

1. Field of the Invention

The present invention relates to a motor-driven fluid pump adapted for delivering fluid into a vessel to be pressurized thereby, and more particularly to such a motor-driven fluid pump provided with a release port for rapidly releasing the pressurized fluid out of the vessel.

2. Description of the Prior Art

In recent years, there have been a growing demand of providing an automated blood pressure measuring device which incorporates a motor-driven fluid pump for feeding pressurized air into an inflatable cuff to be wrapped around the arm of the subject. One such fluid pump for the blood pressure measuring device is disclosed in Japanese Pat. Pub. No. 60-40293 in which a reversible motor has its output shaft connected to a diaphragm member defining a pump chamber through the driving linkage capable of translating the rotary motion of the motor into corresponding reciprocating motion of the diaphragm and vice versa. The driving linkage also connects the motor output shaft to a release valve in such a way as to keep the release valve closed in response to the motor being driven to rotate in the forward direction of pumping up the cuff pressure and to open the release valve in response to the motor being driven to rotate in the reverse direction, allowing a rapid discharge of the pressurized air from the cuff in an automated manner of reversing the motor. In this prior device, when the motor is stopped after attaining a sufficient increase of the cuff pressure with the diaphragm being held in a position of minimizing the volume of the pump chamber, the diaphragm will receive a counter force from the pressurized air to be forced back to its opposite position of maximizing the volume of the pump chamber. Upon this occurrence, the reciprocating motion of the diaphragm may cause the motor output shaft to rotate in the reverse direction through the driving linkage permitting the reverse translation of the reciprocating motion of the diaphragm into the rotating motion of the motor, resulting in an unintended opening of the release valve and therefore rendering the blood pressure measurement totally inoperative. This poses a critical problem in adapting the motor-driven fluid pump for an automated blood pressure measuring device. It is therefore highly desirable for the motor-driven fluid pump of this application to prevent the accidental opening of the release valve while enabling the release valve to be actuated in response to the reversal of the motor.

SUMMARY OF THE INVENTION

The present invention eliminates the above problem and provides a motor-driven fluid pump capable of being successfully incorporated in a blood pressure measuring device. A motor-driven fluid pump in accordance with the present invention comprises a housing with a pump chamber, a pumping member defining the boundary of the pump chamber, and a reversible motor for driving the pumping member in a reciprocating manner in order to draw a fluid through an intake port into the pump chamber and discharge the pressurized fluid through a discharge port into a vessel, such as an inflatable cuff to be pressurized thereby. A driving linkage operatively connects the output shaft of the motor to the pumping member for translation between the rotary motion of the motor output shaft and reciprocating motion of the pumping member.

Included in the fluid pump is a release port with a release valve which is provided in the fluid path between the pump chamber and the vessel for rapid release of the pressurized fluid out of the vessel. The release valve is operatively connected to the motor through a valve actuation means so as to be held closed when the motor is driven to rotate in the forward direction and opened when the motor is driven to rotate in the reverse direction. The characterizing feature of the present invention resides in that the valve actuation means comprises delay means which provides a delayed response action in opening the release valve upon the reversal of the rotating direction of said output shaft from the forward direction to the reverse direction. This delayed response is such that the initiation of opening the release valve is inhibited until the output shaft rotates in the reverse direction through an angle of more than 180 degrees from the reversing point, whereby inhibiting an unintended opening of the release valve due to the reverse translation of the reciprocating motion of the pumping member to the rotary motion of the output.

In other words, the delayed response of the valve actuation means provides an angular margin of more than 180 degrees within which the motor output shaft can freely rotate in the reverse direction without actuating the release valve. This provision of the angular margin presents a safeguard against the unintended opening of the release valve which would take place when the pumping member is forced back in a kickback manner by the presence of the pressurized fluid in the pump chamber as accompanying the corresponding reverse rotary motion of the motor output shaft through the driving linkage. In fact, the pumping member has a greater chance of being stopped at a position of reducing the volume of the pump chamber and therefore receive a kickback force by the pressurized fluid to be thereby forced to the position of maximizing the volume of the pump chamber as accompanying the reverse rotation of the output shaft through a maximum angle of 180 degrees, which reverse rotation would initiate to open the release valve. Nevertheless, the above angular margin ensures that the output shaft can rotate through this angle of 180 degrees without actuating to open the release valve, thus preventing the accidental opening of the release valve within this angular movement of the motor shaft caused by the kickback movement of the pumping member and enabling the release valve to open in response to the subsequent reversal rotation of the motor output shaft caused by energizing the motor. Consequently, when the pumping member is stopped at a position of reducing the volume of the pump chamber in response to the deenergization of the motor so that the pump member is forced back to its position of maximizing the volume of the pump chamber in a kickback manner by the presence of the pressurized fluid in the chamber, the output shaft is driven by the pumping member to rotate through a maximum angle of 180 degrees without actuating as accompanying the corresponding reverse rotation through a maximum angle of 180 degrees, the motor output shaft can freely rotate through this angle of 180 degrees without actuating to open the release valve, thus preventing the accidental opening of the release valve within this angular movement of the motor shaft caused by the kickback movement of the pumping member and enabling the release valve to open in response to the subsequent reversal rotation of the motor output shaft caused by energizing the motor.

Accordingly, it is a primary object of the present invention to provide a motor-driven fluid pump which is capable of compensating for the kickback movement of the pumping member to prevent the accidental opening of the release valve due to such kickback movement while ensuring to actuate the opening of the release valve in response to the reversal of the motor, enhancing the reliability of the pumping operation.

In a preferred embodiment, the valve actuator means comprises a contractible and expandable coil spring wound around the output shaft of the motor. The coil spring has a normal diameter that is less than the diameter of the output shaft so as to be frictionally engaged with the output shaft. Provided with the coil spring are first and second ends which extends radially outwardly to be engageable with the release valve for actuating the release valve between its open and closed positions. The coil spring is driven through the frictional engagement by the output shaft to rotate together therewith such that when the coil spring rotates in the forward direction said first end of the coil comes in engagement with the release valve in its open position so as to actuate it to its closed position and that when the coil spring rotates in the reverse direction said second end of the coil spring comes in engagement with the release valve in the closed position so as to actuate it to its open position. The first and second ends of the coil spring are cooperative with the release valve such that, when the coil spring is driven to rotate together with the output shaft in the forward direction, the second end comes in engagement with the release valve in its closed position to receive a slackening torque therefrom. This slackening torque will act to unwind the coil spring for disengaging the driving connection between the coil spring and the output shaft to thereby permit continuous rotation of the output shaft while keeping the second end engaged with the release valve to positively hold the second end at a fixed angular position about the axis of the output shaft. When the coil spring is driven to rotate in the reverse direction after the closure of the release valve, the second end will rotate in the reverse direction through an angle of more than 180 degrees from said fixed angular position until it comes in engagement with the release valve for reopening the release valve, whereby inhibiting an unintended opening of the release valve due to the kickback movement of the pumping member, that is, the reverse translation of the reciprocating motion of the pumping member to the rotary motion of the output shaft. It is therefore another object of the present invention to provide a motor-driven fluid pump in which a single coil spring is utilized as the release valve actuation means to effectively prevent the unintended opening of the release valve at a simple construction. The first and second ends of the coil spring are also cooperative respectively with first and second legs formed at one end of the release valve so as to perform the following operations. When the first end of the coil spring comes in engagement with the first leg of the release valve in its open position as a consequence of being driven to rotate together with the output shaft in the forward direction, the first end receives from the first leg a counter force which acts to tighten the coil spring and thereby causes it to firmly grip the output shaft, allowing the first end to further rotate together with the output shaft in the forward direction at an increased rate of torque transmission therebetween for initiating the closing of the release valve. When the second end of the coil spring comes in engagement with the first leg of the release valve in its closed position as a consequence of being driven to rotate together with the output shaft in the reverse direction, the second end receives from the second leg a counter force which acts to tighten the coil spring and thereby causes it to firmly grip the output shaft, allowing the second end to further rotate together with the output shaft in the reverse direction at an increased rate of torque transmission therebetween for initiating the opening of the release valve. Thus, the coil spring can respond to the position of the release valve for changing its position in a successful manner with increased torque transmission through the coil spring between the motor output shaft and the release valve. It is therefore a further object of the present invention to provide a motor-driven fluid pump in which the coil spring is cooperative with the release valve to effect the opening and closing of the release valve in a reliable manner.

In a modified form of the present invention, the release valve actuator means comprises a pair of first and second coil springs which are contractible and expandible and wound around the output shaft of the motor in a spaced relation along the axis of the output shaft. Each coil spring has a normal diameter that is less than the diameter of the output shaft so as to be frictionally engaged with the output shaft. The first coil spring has a first end extending from one end thereof radially outwardly to be engageable with the first leg of the release valve for actuating the release valve to its closed position from its open position, while the second coil spring has a second end extending from one end thereof radially outwardly to be engageable with the second leg of the release valve for actuating the release valve to its open position from its closed position. With this separate provision of the first and second coil springs, one of the coil springs can be free from the vibration to which the other coil spring is subjected when the latter coil spring has its end engaged with the corresponding leg of the release valve as repeating to be tightened and loosened on the motor output shaft, keeping the fatigue of the coil springs at a minimum. It is therefore a still further object of the present invention to provide a motor-driven fluid pump in which a pair of coil springs are utilized as the release valve actuator means so as to reduce the fatigue of the coil springs, improving the long-term durability and enhancing the reliability of the pump operation. In the present invention, there are disclosed other advantageous features which include the provisions of the various shapes of the coil spring, and of stopper and latch means incorporated for stably holding the release valve in its open and closed positions. These and other advantageous features will become more apparent from the following detailed description of the embodiments when taken in conjunction with the accompanying drawings.

BRIEF DESCRIPTION OF THE DRAWINGS FIG. 1 is a perspective view of a motor-driven fluid pump in accordance with a first embodiment of the present invention; FIG. 2 is a sectional view taken along the line 2—2 of FIG. 1;

FIGS. 4A to 4D are schematic views for sequentially explaining the closing motion of a release valve of the fluid pump of FIG. 1;

FIGS. 5A to 5D are schematic views for sequentially explaining the opening motion of the release valve of the fluid pump of FIG. 1;

FIGS. 7A to 7D are schematic views for sequentially explaining the closing motion of the release valve in accordance with a second modification of FIG. 1;

DETAILED DESCRIPTION OF THE PREFERRED EMBODIMENTS

Figure 1:
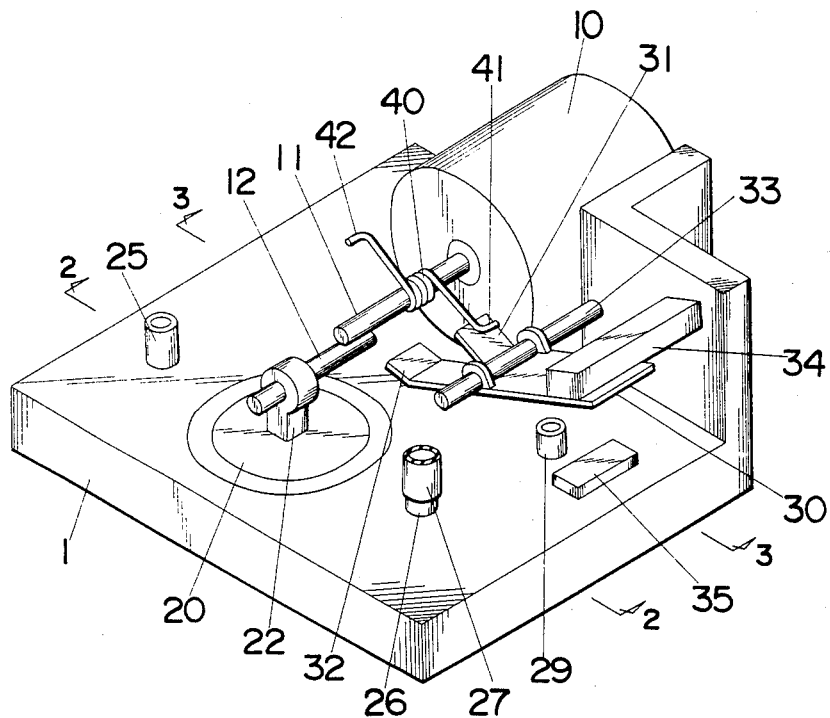
Figure 2:
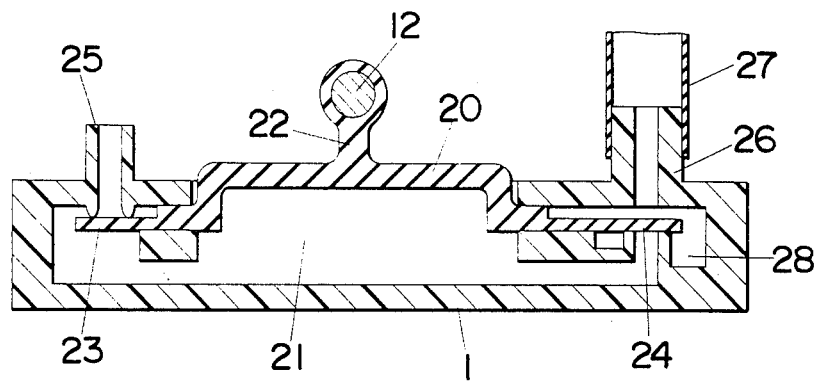
Figure 3:
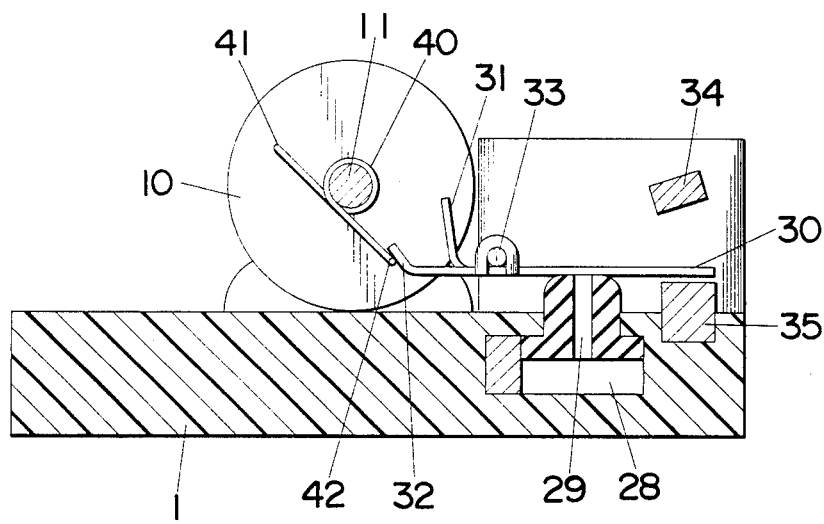
FIG. 3 is a sectional view taken along the line 3—3 of FIG. 1.

Referring to FIG. 1, there is shown a fluid pump in accordance with a preferred embodiment of the present invention which is adapted in use to feed pressurized air into a vessel such as an inflatable cuff of a blood pressure measuring device. The fluid pump includes a housing 1, a reversible electric motor 10 mounted on the housing 1, and a flexible diaphragm 20 employed as a pumping member and peripherally mounted in the housing 1 to define a pump chamber 21 within the housing 1. The electric motor 10 has an output shaft 11 being rotatable in either of the forward or reverse direction. The foremost portion of the output shaft 11 is welded together with an eccentric shaft 12 extending forward in parallel relation therewith to form a crank. Integrally formed on the center of the diaphragm 20 is a connection stem 22 with a bearing hole through which the eccentric shaft 12 extends so as to establish between the output shaft 12 and the diaphragm 20 a driving connection capable of translating the rotary motion of the electric motor 10 into corresponding reciprocating motion of the diaphragm 20. As shown in FIG. 2, the diaphragm 20 is integrally formed at its diametrically opposed portions with an intake valve 23 and a discharge valve 24 which are respectively seated against an inlet port 25 and an outlet port 26 formed in the housing 1. Thus, upon reciprocation of the diaphragm 20, the pump chamber 21 repeats to draw outside air into the pump chamber 21 through the intake port 25 and expel the pressurized air into the cuff through the outlet port 26 and through a flexible tubing 27 connected thereto. It is noted here that the eccentric shaft 12 may be formed by bending the output shaft 11. The intake and the discharge valves 23 and 24 may be separately formed from the diaphragm 20, while the intake and the outlet ports 25 and 26 may be provided either in the upper or lower surface of the housing 1. On the other hand, liquid material may substituted for outside air. Also provided with the housing 1 is a release port 29 for releasing the cuff pressure therethrough. The release port 29 is located in the fluid path between the discharge valve 24 and the cuff and is communicated therewith through a passage 28 extending within the housing 1 and terminating at a portion downstream of the discharge valve 24, as shown in FIG. 2. The release port 29, which is made of a resilient material such as rubber and protrudes on the surface of the housing 1, is closed and opened by a release valve 30 pivotally supported on the housing 1 by a pivot pin 33 extending in parallel relation with the motor output shaft 11. The release valve 30 is in the form of an elongated plate having one end thereof assigned to close the release valve 30. The release valve 30 is operatively connected to the motor output shaft 11 and is controlled thereby to pivot about the pivot pin 33 for limited angular movement between an open position for opening the release port 29 and a closed position for closing the same. A pair of upper and lower stopper magnets 34 and 35 are cooperative with the release valve 30 to define the angular movement of the release valve 30 as well as to stably hold it in both of the open and closed positions by magnetic attraction interacting between the stopper magnets 34 and 35 each made of a permanent magnet and the release valve 30 made of magnetic material. The other end of the release valve 30 is bifurcated to have a first leg 31 and a second leg 32 which are spaced laterally and angled differently with respect to the length of the release valve 30. It is noted here that the release port 29 may be made of any material other than rubber, while the upper and the lower stopper magnets 34 and 35 may be made of magnetizable material with the release valve 30 being correspondingly made of a magnet. On the other hand, the legs 31 and 32 of the release valve 30 may either be formed integrally with or independently of the release valve 30. A coil spring 40 is wound around the motor output shaft 11 to establish a driving connection from the output shaft 11 to the release valve 30 for controlling to actuate the release valve 30 between the closed and open positions in response to the rotating direction of the motor output shaft 11. The coil spring 40 has a first end 41 and a second end 42 extending radially outwardly in generally diametrically opposed directions. The coil spring has a normal diameter slightly less than that of the output shaft 11 so that it is rotatable together therewith through the frictional engagement therebetween.

As schematically shown in FIGS. 4 and 5, the first and second ends 41 and 42 of the coil spring 40 trace the corresponding circular paths M and N upon rotation of the motor output shaft 11, and are cooperative respectively with the first and second legs 31 and 32 of the release valve 30 in such a relation that they come in engagement respectively with the first and the second legs 31 and 32 to actuate the release valve 30 in the following manner. It should be noted here that although the circular paths M and N are depicted to have different diameters for the sake of facilitating explanation, they can be rendered same.

Reference is firstly made for the closing mode of the release valve 30 based on FIGS. 4A, 4B, 4C and 4D illustrating in a sequence changing positions of the coil spring 40 and the release valve 30.

In FIG. 4A, the release valve 30 is held in its open position with the first leg 31 projecting into the circular path M of the first end 41 and with the second leg 32 being put out of the circular path N of the second end 42. When the motor output shaft 11 rotates in the forward direction for driving the coil spring 40 to rotate in the counterclockwise direction C, as viewed in the figures, from the position of FIG. 4A, the first end 41 comes in engagement with the first leg 31 after rotating substantially 360 degrees (exactly somewhat less than 360 degrees) in angle, as shown in FIG. 4B. Once the first end 41 is engaged with the first leg 31, it receives a counter force from the release valve 30 held in the open position by the magnetic force as it continue to rotate in that direction. This counter force acts to wind and therefore tighten the coil spring 40 on the output shaft 11 so as to develop therebetween an increased torque transmission enough for overcoming the latching force of holding the release valve 30 in the open position, thereby forcing the release valve 30 to move to the closed position as disengaging the release valve 30 from the upper stopper magnet 34, as shown in FIG. 4C. After completing the closure of the release valve 30, further rotation of the coil spring 40 in the same direction will cause the second end 42 to become engaged with the second leg 32 now projecting in the circular path N, as shown in FIG. 4D. Upon this engagement, the second end 42 receives the same counter force from the release valve 30 held in the closed position. However, the counter force acts to unwind or slacken the coil spring 40 in contrast to the above, thereby disengaging the coil spring 40 from the output shaft 11 and allowing the output shaft 11 to continue rotating in the same direction while keeping the second end 42 at the fixed position of being engaged with the second leg 32 as shown in FIG. 4D. In detail, the coil spring 40 repeats loosening and tightening on the output shaft 11 to positively keep the second end 42 at that fixed angular position as the output shaft 11 continues to rotate in the same direction. The opening mode of the release valve 30 is now explained with reference to FIGS. 5A, 5B, 5C and 5D illustrating in a sequence changing positions of the coil spring 40 and the release valve 30.

When the output shaft 11 is reversed for driving the coil spring 40 to rotate in the clockwise direction O from the position of FIG. 5A which is identical to FIG. 4D in which the release valve 30 is held in its closed position with the first leg 31 being put out of the circular path M of the first end 41 and with the second leg 32 projecting into the circular path N of the second end 42, the coil spring 40 rotates somewhat less than 360 degrees but more than 180 degrees in angle before the second end 42 comes in engagement with the second leg 32, as shown in FIG. 5B. Once this engagement occurs, the second end 42 receives a counter force from the release valve 30 held in the closed position by magnetic force from the lower stopper magnet 35 as it continues to rotate in the same direction O. This counter force acts to wind or tighten the coil spring 40 on the output shaft 11 so as to develop therebetween an increased torque transmission enough for overcoming the latching force of holding the release valve 30 in the closed position, thereby forcing the release valve 30 to move to the open position as disengaging the release valve 30 from the lower stopper magnet 35, as shown in FIG. 5C. After completing the opening of the release valve 30, further rotation of the coil spring 40 in the same direction O will cause the first end 41 instead to become engaged with the first leg 31 now projecting in the circular path M, as shown in FIG. 5D. Upon this engagement, the first end 41 receives the same counter force from the release valve 30 held in the open position. However, the counter force acts to unwind or slacken the coil spring 40 to thereby disengage the coil spring 40 from the output shaft 11, allowing the output shaft 11 to continue rotating in the same direction O while keeping the first end 41 at the fixed position of being engaged with the first leg 31 as shown in FIG. 5D. It should be noted at this point that the opening of the release valve 30 can be only effected after reversing the motor and the coil spring through an angle of more than 180 degrees in angle (from the position of FIG. 5A to that of FIG. 5B), since the coil spring 40 is always kept at the position of FIG. 5A after closing the release valve 30. Consequently, even when the diaphragm 20 is stopped at a position of minimizing the volume of the pump chamber 21 such that it is blown back by a pressurized air in the chamber 21 in a kickback manner to a position of maximizing the volume of the pump chamber 21 as accompanying the corresponding reverse rotation of output shaft 11 and the coil spring 40 by a maximum angular displacement of 180 degrees, the coil spring 40 is refrained from actuating the release valve 30 to open through this angular displacement, thus compensating for any kickback effect which is likely to take place when the diaphragm 20 is stopped at a position of reducing the volume of the pump chamber 21 and preventing an accidental or unintended opening of the release valve 30 due to such kickback effect.

Figure 6A:
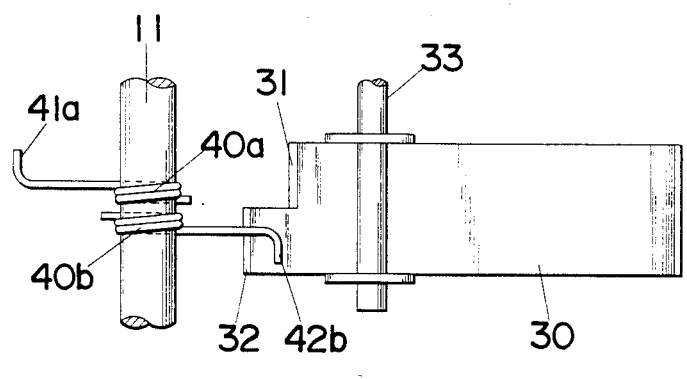
FIG. 6A is a partial plan view showing a pair of coil springs and a release valve to be actuated thereby in accordance with a first modification of the present invention.
Figure 6B:
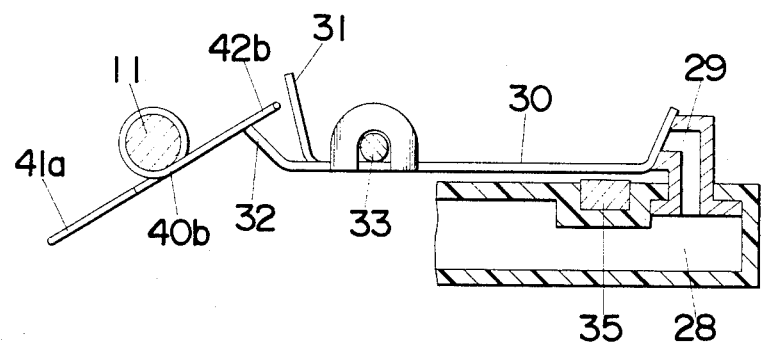
FIG. 6B is a partial view partly in cross section of the combination of the coil springs and the release valve of FIG. 6A.
Figure 8A:
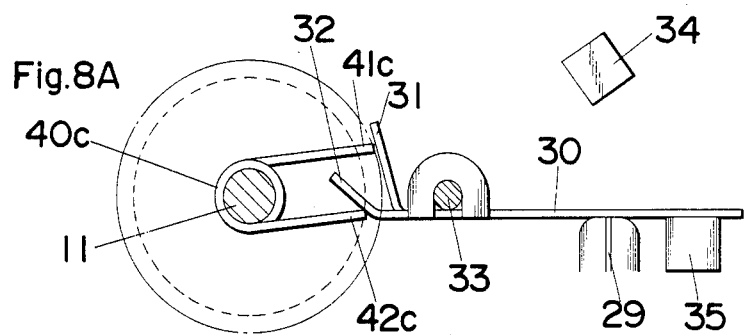
FIGS. 8A to 8D are schematic views for sequentially explaining the opening motion of the release valve of the second modification.
Figure 8B:
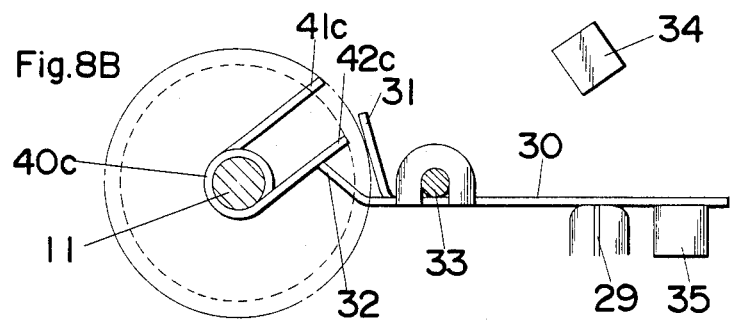
Figure 8C:
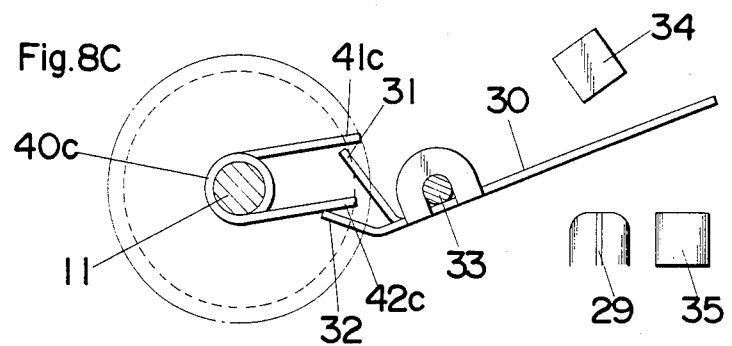
Figure 8D:
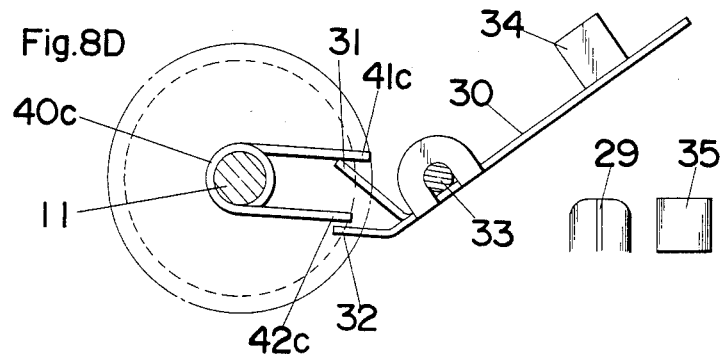
Figure 9A:
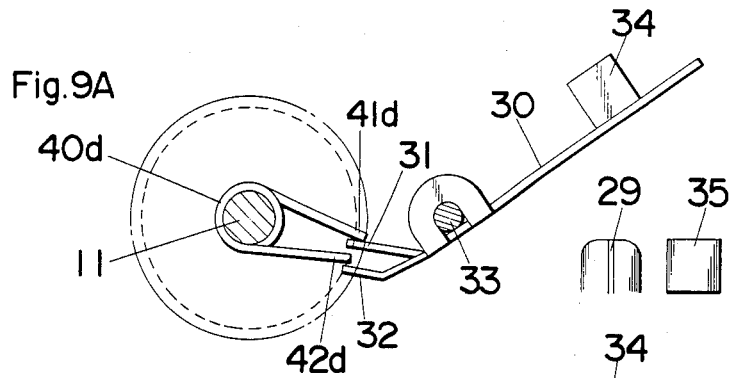
FIGS. 9A to 9D are schematic views for sequentially explaining the closing motion of the release valve in accordance with a third modification of FIG. 1.
Figure 9B:
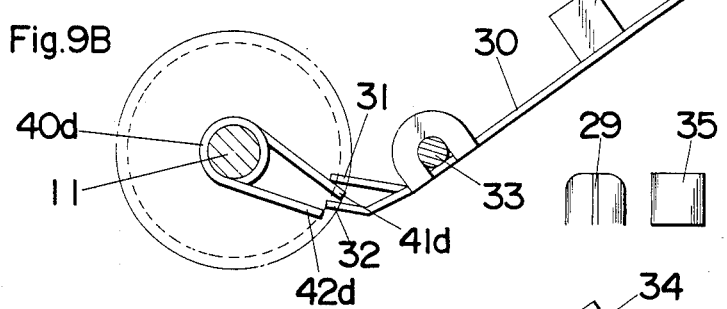
Figure 9C:
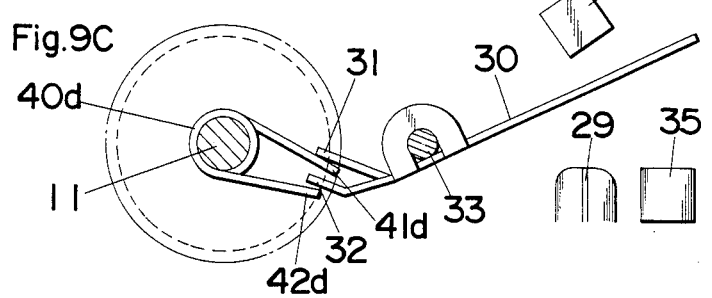
Figure 9D:
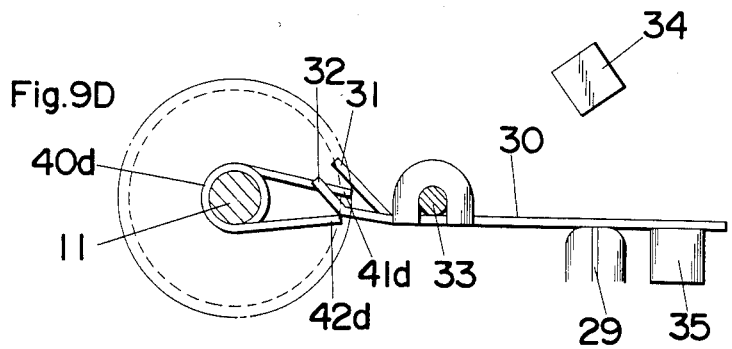
Figure 10A:
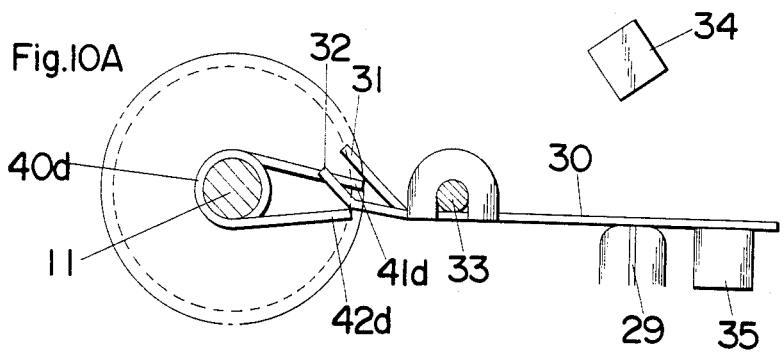
FIGS. 10A to 10D are schematic views for sequentially explaining the opening motion of the release valve of the thir modification.
Figure 10B:
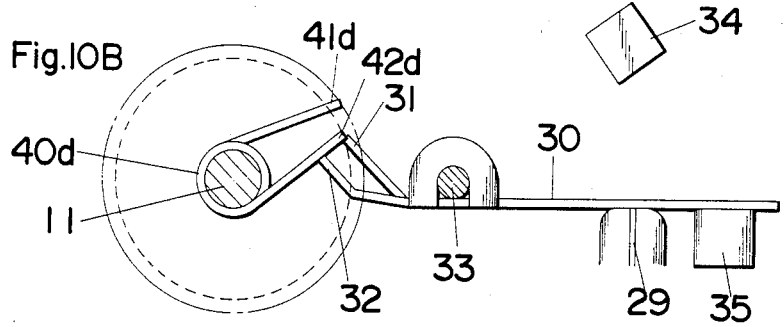
Figure 10C:
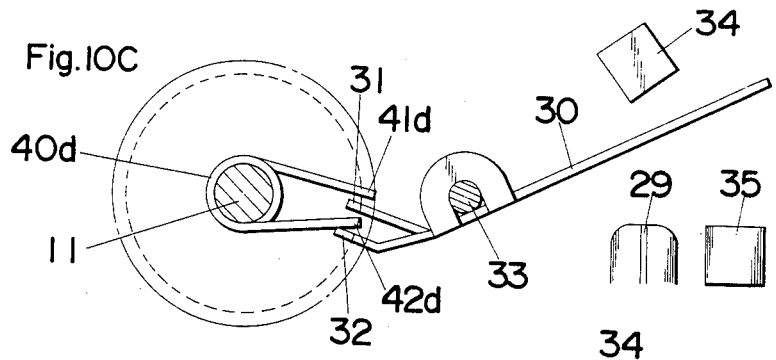
Figure 10D:
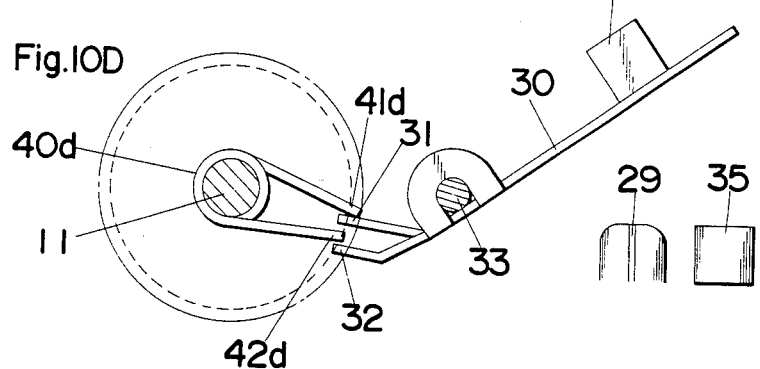

Referring to FIGS. 6A and 6B, there is shown a first modification of the above embodiment in which a pair of separately formed first and second coil springs 40a and 40b are employed instead of the single coil spring 40. The first and second coil springs 40a and 40b, each having at its end longer and shorter radial extensions, are wound around the output shaft 12 and axially spaced therealong with the shorter extensions opposed in a closely adjacent relations, as shown in FIG. 6A. The longer extension of the first coil spring 40a defines a first end 41a engageable with the first leg 31 of the release valve 30, while the longer one of the second coil spring 40b defines a second end 42b engageable with the second leg 32 of the release valve 30. The operation of the first and second coil springs 40a and 40b in combination is identical with that of the first embodiment in actuating the release valve 30 for movement between the closed and open positions, but differs in that one of the first and second springs 40a and 40b can be isolated from the other when the latter repeats loosening and tightening on the output shaft 11 as a consequence of the first or second end being engaged with the corresponding legs of the release valve 30 and receiving a slackening force as a counter force from the release valve 30. With this result, one of the coil springs 40a and 40b is kept free from the vibration which the other coil spring suffers when repeating the loosening and tightening, causing substantially no critical fatigue to be developed due to such vibration and resulting in an enhanced durability and reliability. It is noted at this point that the shorter extensions of the coil springs 40a and 40b are cut as short as possible so as not to act to impart any detrimental vibratory motion which would cause critical torsional fatigue in each coil spring. It is further noted that the end portion of the release valve 30 assigned to close the release port 29 is angled upward with respect to the length thereof so as to make an effective sealing contact with correspondingly angled uppermost portion of the release port 29.

Although the above embodiment and its modification utilizes a coil spring or coil springs having the first end and the second end extending in generally opposite directions, the present invention is not limited thereto and may utilize other shapes of the coil spring as shown in the following modifications featuring the coil springs having the first and second ends extending generally in the same direction. One such modification is shown in FIG. 7, composed of FIGS. 7A, 7B, 7C, and 7D and 8, composed of FIGS. 8A, 8B, 8C and 8D, and the other modification is shown in FIG. 9, composed of FIGS. 9A, 9B, 9C, and 9D and 10, composed of FIGS. 10A, 10B, 10C and 10D. In the modification of FIGS. 7 and 8, the coil spring 40c has the first and second ends 41c and 42c extending in generally parallel relation to each other for engagement with the corresponding first and second legs 31 and 32 of the release valve 30. In the modification of FIGS. 9 and 10, the coil spring 40d has the first and second ends 41d and 42d extending in a radially outwardly closing relation for engagement with the corresponding first and second legs 31 and 32 of the release valve 30. The operation of each of the coil springs 40c and 40d is identical to that of the first embodiment and is easily understood from FIGS. 7 and 8, and from FIGS. 9 and 10, which are arranged in exact correspondence to FIGS. 4 and 5 of the first embodiment. It is to be noted that also in these modifications each of the coil springs 40c and 40d can be held at a fixed angular position (see FIGS. 8A and 10A) after completing the closure of the release valve 30 and requires to reversely rotate more than 180 degrees in angle before the second end 42c or 42d comes in engagement with the second leg 32 to initiate the opening of the release valve (see FIGS. 8B and 10B), successfully preventing the accidental and unintended opening of the release valve 30 due to the kickback effect of the diaphragm 20, in the same manner as in the previous embodiment.

Figure 11A:
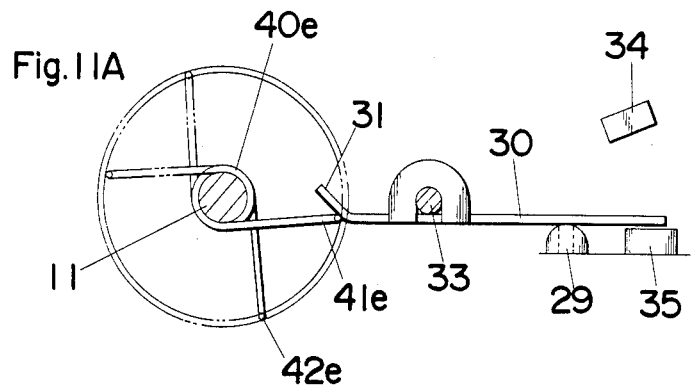
FIGS. 11A and 11B are schematic views respectively showing operation of a coil spring and a release valve to be actuated thereby in accordance with a fourth modification of FIG. 1.
Figure 11B:
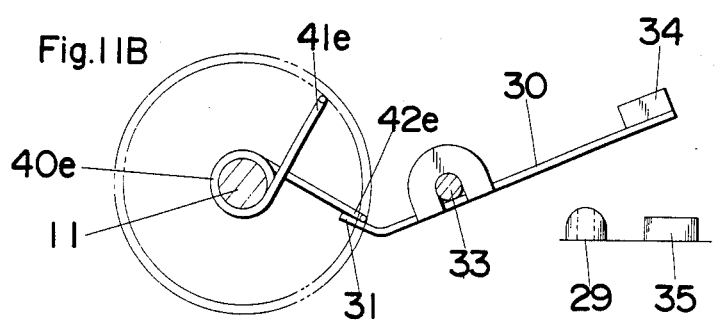

Referring to FIGS. 11A and 11B, there is shown a further modification of the first embodiment which utilizes a coil spring 40e having its first and second ends 41e and 42e crossed with each other. In this modification, the release valve 30 is formed with a single leg 31 responsible for engagement with each of the first and second ends 41e and 42e. FIG. 11A shows a condition where the coil spring 40e is kept at a fixed position after closing the release valve 30. In this condition, the coil spring 40e repeats being engaged with and disengaged from the output shaft 11 as the first end 41e engaged with the release valve 30 receives therefrom a counter force acting to slacken the coil spring 40e. When the output shaft 11 is reversely rotated in the clockwise direction for opening the release valve 30, the second end 42e comes in engagement with the release valve 30 at the leg 31 to open the release valve 30, as shown in FIG. 11B. It is to be noted at this point that although the second end 42e is engaged with the release valve 30 in such a manner as to receive a counter force acting to slacken the coil spring 40e, the coil spring 40e is selected to have a torsional resistance greater enough for overcoming the counter force produced in unlatching the release valve 30 from the closed position of FIG. 11A against the magnetic force exerted from the lower stopper magnet 35, thus allowing the coil spring 40e to remain engaged with the output shaft 11 and therefore to rotate in the clockwise direction together therewith for completing the opening of the release valve 30. Once the release valve 30 is opened with its end abutted against the upper stopper magnet 34, as shown in FIG. 11B, the counter force becomes increased to such an extent that the coil spring 40e no longer overcome and therefore the coil spring 40e is slackened thereby to be disengaged from the output shaft 11, allowing the output shaft 11 to freely rotate in the same direction. The same applies for closing the release valve 30 from the position of FIG. 11B to that of FIG. 11A. As apparent from the above, this modification can also provide that the coil spring 40e is required to reversely rotate through an angle of more than 180 degrees before it initiates to open the release valve, compensating for the kickback effect of the diaphragm to prevent the accidental opening of the release valve 30, as discussed previously.

It is noted incidentally with regard to all the embodiment and the modifications that the electric motor 10 may be deenergized after the release valve 30 is put in the open position thereof.

What is claimed is:

1. In a fluid pump for delivering fluid into a vessel to be pressurized thereby comprising:

a housing with an intake port and a discharge port;

a pump chamber formed in the housing in fluid communication with the intake port and the discharge port;

a pumping member defining a boundary of the pump chamber and movable in a reciprocatory manner between a first position of expanding the pump chamber and a second position of contracting the pump chamber;

a reversible electric rotary motor having an output shaft;

driving linkage means operatively connecting the output shaft of the motor and the pumping means so as to translate the rotary motion of the output shaft into a reciprocating motion of the pumping member between said first and second position for alternately drawing fluid into the pump chamber through said intake port and discharging the fluid through the discharge port, said drive linkage means allowing the reverse translation of the reciprocating motion of the pumping member to the rotary motion of the output shaft when the motor stops rotating;

a release port in a fluid path downstream of said discharge port for rapidly releasing pressurized fluid, said release port being provided with a release valve movable between a closed position and an open position; and release valve actuation means operatively connected to the output shaft of the motor to be driven thereby for actuating said release valve into the closed position upon the output shaft being rotated in the forward direction and actuating said release valve into the open position upon the output shaft being rotated in the reverse direction; the improvement comprising:

said valve actuation means including delay means which provides a delayed response action in opening the release valve upon the reversal of the rotating direction of said output shaft from the forward direction to the reverse direction, said delayed response being such that the initiation of opening the release valve is inhibited until the output shaft rotates in the reverse direction through an angle of more than 180 degrees from the reversing point, whereby inhibiting an unintentional opening of the release valve due to said reverse translation of the reciprocating motion of the pumping member to the rotary motion of the output shaft.

2. A fluid pump for delivering fluid into a vessel to be pressurized thereby comprising in combination:

a housing with an intake port and a discharge port;

a pump chamber formed in the housing in fluid communication with the intake port and the discharge port;

a pumping member defining a boundary of the pump chamber and movable in a reciprocatory manner between a first position of expanding the pump chamber and a second position of contracting the pump chamber;

a reversible electric rotary motor having an output shaft;

driving linkage means operatively connecting the output shaft of the motor and the pumping member so as to translate the rotary motion of the output shaft into a reciprocating motion of the pumping member between said first and second positions for alternately drawing fluid into the pump chamber through said intake port and discharging the fluid through the discharge port, said drive linkage means allowing the reverse translation of the reciprocating motion of the pumping member to the rotary motion of the outpout shaft when the motor stops rotating;

a release port in a fluid path downstream of said discharge port for rapidly releasing pressurized fluid, said release port being provided with a release valve movable between a closed position and an open position;

release valve actuation means which responds to the rotating direction of the output shaft for actuating said release valve between its closed and open positions, said release valve actuator means including a contractible and expandable coil spring wound around the output shaft of the motor, and said coil spring having a normal diameter that is less than the diameter of the output shaft so as to be fictionally engaged with the output shaft, and said coil spring having first and second ends respectively extending radially outwardly to be engageable with said release valve for actuating the release valve between its open and closed positions;

said coil spring being driven through said frictional engagement by the output shaft to rotate together therewith such that when the coil spring rotates in the forward direction said first end of the coil comes in engagement with the release valve in its open position so as to actuate it to its closed position and that when the coil spring rotates in the reverse direction said second end of the coil spring comes in engagement with the release valve in the closed position so as to actuate it to its open position; and said first and second ends of the coil spring being cooperative with the release valve such that when the coil spring is driven to rotate together with the output shaft in the forward direction said second end comes in engagement with the release valve in its closed position so as to receive a slackening torque therefrom, which slackening torque acting to unwind the coil spring for disengaging the driving connection between the coil spring and the output shaft to thereby permit continuous rotation of the output shaft while keeping the seocnd end engaged with the release valve to positively hold the second end at a fixed angular position about the axis of the output shaft, and that when the coil spring is driven to rotate in the reverse direction after the closure of the release valve said second end will rotate in the reverse direction through an angle of more than 180 degrees from said fixed angular position until it comes in engagement with the release valve for reopening the release valve, whereby inhibiting an unintentional opening of the release valve due to said reverse translation of the reciprocating motion of the pumping member to the rotary motion of the output.

3. A fluid pump as set forth in claim 2, wherein the release valve is provided at its one end with first and second legs respectively engageable with first and second ends of the coil spring, and wherein when the first end of the coil spring comes in engagement with the first leg of the release valve in its open position as a consequence of being driven to rotate together with the output shaft in the forward direction, the first end receives from the first leg a counter force which acts to tighten the coil spring and thereby causes it to firmly grip the output shaft, allowing the first end to further rotate together with the output shaft in the forward direction at an increased rate of torque transmission therebetween for initiating the closing of the release valve, and when the second end of the coil spring comes in engagement with the first leg of the release valve in its closed position as a consequence of being driven to rotate together with the output shaft in the reverse direction, the second end receives from the second leg a counter force which acts to tighten the coil spring and thereby causes it to firmly grip the output shaft, allowing the second end to further rotate together with the output shaft in the reverse direction at an increased rate of torque transmission therebetween for initiating the opening of the release valve.

4. A fluid pump as set forth in claim 2, wherein said release port is formed in the housing to be located midway in the fluid communicating path between said discharge port and a vessel.

5. A fluid pump as set forth in claim 2, wherein said pumping member is in the form of a flexible and resilient diaphragm which is driven through said driving means to reciprocate for said pumping action.

6. A fluid pump as set forth in claim 2, in combination with a vessel fluidally connected to said discharge port, wherein said vessel is in the form of an inflatable bag adapted to be used as a cuff which is wrapped around the arm of the human subject in a blood pressure measurement.

7. A fluid pump as set forth in claim 2, wherein said release valve is in the form of an elongated member having at its one longitudinal end a flap valve portion which is in and out of sealing engagement with said release port;

the other longitudinal end of the release valve being bifurcated to provide a pair of laterally spaced first and second legs which are differently angled with respect to the length of the release valve;

said release valve being pivotally supported at a portion intermediate its longitudinal ends to be pivotable about a pivot axis for movement between the open and closed positions within a limited angle defined by stopper means;

the first and second ends of said coil spring being spaced along the axis of said output shaft so as to be engageable respectively with said laterally spaced first and second legs of the release valve;

the first and second ends being angularly spaced about the axis of said output shaft so that only one of the first and second ends is engageable with the corresponding one of the first and second legs at a time;

the distal ends of said first and second ends tracing respective circular paths about the axis of said output shaft as the coil spring rotates thereabout;

the coil spring and the release valve being so related that during the course of closing the release valve the second leg of the release valve is kept out of the circular path of the second end of the coil spring until the first leg of the release valve is engaged with the first end of the coil spring rotating in the forward direction to be thereby driven toward its closed position, and that during the course of opening the release valve the first leg is kept out of the circular path of the first end of the coil spring until the second leg of the release valve is engaged with the second end of the coil spring rotating in the reverse direction to be thereby driven toward its open position; and said release valve being associated with latch means to be latched at either of its open or closed position, the latching means being responsible for providing a counter force which is produced when the first end of the coil spring comes in engagement with the first leg as a consequence of being driven to rotate together with the output shaft in the forward direction and which acts on the first end to tighten the coil spring and thereby causes it to firmly grip the output shaft, allowing the first end to further rotate together with the output shaft in the forward direction at an increased rate of torque transmission therebetween for initiating the closing of the release valve against the latching force by the latching means, said latching means being further responsible for providing another counter force which is produced when the second end of the coil spring comes in engagement with the second leg as a consequence of being driven to rotate together with the output shaft in the reverse direction and which acts on the second end to tighten the coil spring and thereby causes it to firmly grip the output shaft, allowing the second end to further rotate together with the output shaft in the forward direction at an increased rate of torque transmission therebetween for initiating the opening of the release valve against the latching force by the latching means, said stopper means being responsible for said slackening torque which is produced when the second end of the coil spring comes in engagement with the second leg of the release valve after being rotated together with the output shaft in the forward direction and which acts on the second end so as to slacken the coil spring and thereby disengages the coil spring from the output shaft, allowing the output shaft to further rotate in the forward direction while keeping the second end of the coil spring engaged with the second leg and holding it at a fixed angular position about the axis of the output shaft, whereby the second end of the coil spring is required to rotate together with the output shaft in the reverse direction through an angle of more than 180 degrees from said fixed angular position before it is again engaged with the second leg of the release valve for reopening the release valve;

said stopper means being further responsible for another slackening torque which is produced when the first end of the coil spring comes in engagement with the first leg after being driven to rotate together with the output shaft in the reverse direction and which acts on the first end so as to slacken the coil spring and thereby disengage the coil spring from the output shaft, allowing the output shaft to further rotate in the reverse direction while keeping the first end of the coil spring engaged with the first leg.

8. A fluid pump as set forth in claim 7, wherein said first and second ends extend substantially diametrically in opposite directions from the axis of the output shaft.

9. A fluid pump as set forth in claim 7, wherein said stopper means comprises a pair of stop pieces which are mounted on the housing in an angularly spaced relationship about the pivot axis of the release valve for limiting the angle within which said release valve is allowed to pivot about the pivot axis for movement between its closed and open positions.

10. A fluid pump as set forth in claim 9, wherein said stop pieces are made of a permanent magnet and said valve member is made of magnetic material attractable to the stop pieces, said stop pieces being cooperative with the valve member to define said latch means for releasably latching the valve member in either of its closed or open position.

11. A fluid pump for delivering fluid into a vessel to be pressurized thereby comprising in combination:

a housing with an intake port and a discharge port;

a pump chamber formed in the housing in fluid communication with the intake port and the discharge port;

a pumping member defining a boundary of the pump chamber movable in a reciprocatory manner between an extended first position of expanding the pump chamber and a second position of contracting the pump chamber;

a reversible electric rotary motor having an output shaft;

driving linkage means operatively connecting the output shaft of the motor and the pumping member so as to translate the rotary motion of the output shaft into a reciprocating motion of the pumping member between said first and second positions for alternatively drawing fluid into the pump chamber through said intake port and discharging the fluid through the discharge port, said drive linkage means allowing the reverse translation of the reciprocating motion of the pumping member to the rotary motion of the output shaft when the motor stops rotating;

a release port in a fluid path downstream of said discharge port for rapidly releasing pressurized fluid, said release port being provided with a release valve movable between a closed position and an open position;

release valve actuation means which responds to the rotating direction of the output shaft for actuating said release valve between its closed and open positions, said release valve actuator means including a pair of first and second coil springs which are contractible and expandable and wound around the output shaft of the motor in spaced relation along the axis of the output shaft, each of said coil springs having a normal diameter than is less than the diameter of the output shaft so as to be fictionally engaged with the output shaft;

said first coil spring having a first end extending from one end thereof radially outwardly to be engageble with said release valve for actuating the release valve to its closed position from its open position, and said second coil spring having a second end extending from one end thereof radially outwardly to be engageable with said release valve for actuating the release valve to its open position from its closed position;

said first and second coil springs being driven through said frictional engagement by the output shaft to rotate together therewith such that when the coil springs rotate in the forward direction said first end of the first coil spring comes in engagement with the release valve in its open position so as to actuate it to its closed position and that when the coil springs rotate in the reverse direction said second end of the second coil spring comes engagement with the release valve in the closed position so as to actuate it to its open position; and said first and seocnd ends of the coils springs being cooperative with the release valve such that when the coil springs are driven to rotate together with the output shaft in the forward direction said second end comes in engagement with the release valve in its closed position so as to receive a slacking torque therefrom, which slackening torque acting to unwind the second coil spring for disengaging the driving connection between the coil spring and the output shaft to thereby permit continuous rotation of the output shaft while keeping the second end engaged with the release valve to positively hold the second end at a fixed angular position about the axis of the output shaft, and that when the coil springs are driven to rotate in the reverse direction after the closure of the release valve said second end will rotate in the reverse direction through an angle of more than 180 degrees from said fixed angular position until it comes in engagement with the release valve for reopening the release valve, whereby inhibiting an unintentional opening of the release valve due to said reverse translation of the reciprocating motion of the pumping member to the rotary motion of the output.

12. A fluid pump as set forth in claim 11, wherein said release port is formed in the housing to be located midway in the fluid communicating path between said discharge port and a vessel.

13. A fluid pump as set forth in claim 11, wherein said pumping member is in the form of a flexible and resilient diaphragm which is driven through said driving means to reciprocate for said pumping action.

14. A fluid pump as set forth in claim 11, in combination with a vessel fluidly connected to said discharge port, wherein said vessel is in the form of an inflatable bag adapted to be used as a cuff which is wrapped around the arm of a human subject in a blood pressure measurement.

15. A fluid pump as set forth in claim 11, wherein said release valve is in the form of elongated member having at its one longitudinal end a flap valve portion which is in and out of sealing engagement with said release port;

the other longitudinal end of the release valve being bifurcated to provide a pair of laterally spaced first and second legs which are differently angled with respect to the length of the release valve;

said release valve being pivotally supported at a portion intermediate its longitudinal ends to be pivotable about a pivot axis for movement between the open and closed positions within a limited angle defined by stopper means;

the first and second ends of the respective coil springs being spaced along the axis of said output shaft so as to be engageable respectively with said laterally spaced first and second legs of the release valve;

the first and second ends being angularly spaced about the axis of said output shaft so that one of the first and second ends is engageable with the corresponding one of the first and second legs at a time;

the distal ends of said first and second ends tracing respective circular path about the axis of said output shaft as the coil spring rotates thereabout;

the first and second coil springs and the release valve being so related that during the course of closing the release valve the second leg of the release valve is kept out of the circular path of the second end of the second coil spring until the first leg of the release valve is engaged with the first end of the first coil spring rotating in the forward direction to be thereby driven toward its closed position, and that during the course of opening the release valve the first leg is kept out of the circular path of the first end of the first coil spring until the second leg of the release valve is engaged with the second end of the second coil spring rotating in the reverse direction to be thereby driven toward its open position; and said release valve being associated with latch means to be latched at either of its open or closed position, the latching means being responsible for providing a counter force which is produced when the first end of the first coil spring comes in engagement with the first leg as a consequence of being driven to rotate together with the output shaft in the forward direction and which acts on the first end to tighten the first coil spring and thereby causes it to firmly grip the output shaft, allowing the first end to further rotate together with the output shaft in the forward direction at an increased rate of torque transmission therebetween for initiating the closing of the release valve against the latching force by the latching means, said latching means being further responsible for providing another counter force which is produced when the second end of the second coil spring comes in engagement with the second leg as a consequence of being driven to rotate together with the output shaft in the reverse direction and which acts on the second end to tighten the second coil spring and thereby causes it to firmly grip the output shaft, allowing the second end to further rotate together with the output shaft in the forward direction at an increased rate of torque transmission therebetween for initiating the opening of the release valve against the latching force by the latching means, said stopper means being responsible for said slackening torque which is produced when the second end of the second coil spring comes in engagement with the second leg of the release valve after being rotated together with the output shaft in the forward direction and which acts on the second end so as to slacken the second coil spring and thereby disengages the second coil spring from the output shaft, allowing the output shaft to further rotate in the forward direction while keeping the second end of the second coil spring engaged with the second leg and holding it at a fixed angular position about the axis of the output shaft, whereby the second end of the second coil spring is required to rotate together with the output shaft in the reverse direction through an angle of more than 180 degrees from said fixed angular position before it is again engaged with the second leg of the release valve for reopening the release valve;

said stopper means being further responsible for another slackening torque which is produced when the first end of the first coil spring comes in engagement with the first leg after being driven to rotate together with the output shaft in the reverse direction and which acts on the first end so as to slacken the first coil spring and thereby disengage the first coil spring from the output shaft, allowing the output shaft to further rotate in the reverse direction while keeping the first end of the first coil spring engaged with the first leg.

16. A fluid pump as set forth in claim 15, wherein said first and second ends extend substantially diametrically in opposite directions from the axis of the output shaft.

17. A fluid pump as set forth in claim 15, wherein said stopper means comprises a pair of stop pieces which are mounted on the housing in an angularly spaced relationship about the pivot axis of the release valve for limiting the angle within which said release valve is allowed to pivot about the pivot axis for movement between its closed and open positions.

18. A fluid pump as set forth in claim 17, wherein said stop pieces are made of a permanent magnet and said valve member is made of magnetic material attractable to the stop pieces, said stop pieces being cooperative with the valve member to define said latch means for releasably latching the valve member in either of its closed or open position.

* * * * *